US008517941B1

(12) United States Patent
Wenzel

(10) Patent No.: US 8,517,941 B1
(45) Date of Patent: Aug. 27, 2013

(54) IMPLANTABLE CARDIAC DEVICE AND METHOD FOR MONITORING BLOOD-GLUCOSE CONCENTRATION

(75) Inventor: Brian Jeffrey Wenzel, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1702 days.

(21) Appl. No.: 11/877,004

(22) Filed: Oct. 23, 2007

(51) Int. Cl.
A61B 5/02 (2006.01)

(52) U.S. Cl.
USPC .......................................... 600/365

(58) Field of Classification Search
USPC .................. 600/372–374, 377, 365
See application file for complete search history.

(56) References Cited

U.S. PATENT DOCUMENTS

| 4,686,988 A | 8/1987 | Sholder |
| 4,708,142 A | 11/1987 | DeCote, Jr. |
| 4,729,376 A | 3/1988 | DeCote, Jr. |
| 4,731,051 A | 3/1988 | Fischell |
| 4,809,697 A | 3/1989 | Causey, III et al. |
| 4,869,254 A | 9/1989 | Stone et al. |
| 4,944,299 A | 7/1990 | Silvian |
| 4,947,845 A | 8/1990 | Davis |
| 4,969,467 A | 11/1990 | Callaghan et al. |
| 5,078,136 A | 1/1992 | Stone et al. |
| 5,350,410 A | 9/1994 | Kleks et al. |
| 5,387,327 A * | 2/1995 | Khan ........................... 600/347 |
| 6,181,958 B1 * | 1/2001 | Steuer et al. .................. 600/322 |
| 6,275,734 B1 | 8/2001 | McClure et al. |
| 6,491,639 B1 | 12/2002 | Turcott |
| 6,731,967 B1 | 5/2004 | Turcott |
| 6,997,879 B1 | 2/2006 | Turcott |
| 2003/0004423 A1 * | 1/2003 | Lavie et al. .................... 600/500 |
| 2003/0125612 A1 * | 7/2003 | Fox et al. ....................... 600/347 |
| 2003/0199925 A1 * | 10/2003 | Houben ........................... 607/2 |
| 2004/0079652 A1 * | 4/2004 | Vreeke et al. ............. 205/777.5 |
| 2006/0281187 A1 * | 12/2006 | Emery et al. ................... 436/169 |

OTHER PUBLICATIONS

Alexakis et al., "A Knowledge-Based Electrocardiogram-Monitoring System for Detection of the Onset of Nocturnal Hypoglycaemia in Type 1 Diabetic Patients," Computers in Cardiology 33:5-8 (2006).
Bornzin et al., "Measuring Oxygen Saturation and Hematocrit Using a Fiberoptic Catheter", IEEE/9th Annual Conf. of the Eng. & Biol. Soc. (1987).
Collier et al., "Transient Atrial Fibrillation Precipitated by Hypoglycaemia: Two Case Reports," Postgraduate Medical Journal 63:895-897 (1987).

(Continued)

*Primary Examiner* — Patricia Mallari
*Assistant Examiner* — Vasuda Ramachandran
(74) *Attorney, Agent, or Firm* — Theresa Raymer; Steven M. Mitchell

(57) ABSTRACT

An implantable medical device, implantable cardiac stimulation device, implantable defibrillator or pacemaker provides continuous monitoring of blood-glucose concentration in the blood of a patient. Blood-glucose concentration and blood-glucose concentration trends are calculated by measuring changes in the hematocrit of the patient. An external blood-glucose monitor may be used to provide blood-glucose calibration values to the implantable device to enhance accuracy of blood-glucose concentration values. The implantable device compares the blood-glucose concentration and/or concentration trends with acceptable limits and generates appropriate warning signals. The implantable device may optionally control one or more therapeutic devices to maintain blood-glucose concentration within an acceptable range. The enhanced control of blood-glucose concentration reduces the risk of arrhythmia and enhances the effectiveness of cardiac pacing and/or defibrillation.

17 Claims, 7 Drawing Sheets

(56) References Cited

OTHER PUBLICATIONS

Greenberg et al., "Analysis of Mortality Events in the Multicenter Automatic Defibrillator Implantation Trial (MADIT-II)," JACC 43:1459-65 (2004).

Koivikko et al., "Effects of Sustained Insulin-Induced Hypoglycemia on Cardiovascular Autonomic Regulation in Type 1Diabetes," Diabetes 54:744-750 (2005).

Lee et al., "Influence of Autonomic Neuropathy on QTc Interval Lengthening During Hypoglycemia in Type 1 Diabetes," Diabetes 53:1535-1542 (2004).

Rokas et al., "Proarrhythmic Effects of Reactive Hypoglycemia," PACE 15:373-376 (1992).

Shimada et al., "Arrythmia During Insulin-Induced Hypoglycemia in a Diabetic Patient," Arch. Intern. Med. 144:1068-69 (1984).

Steinke et al., "Reflectance Measurements of Hematocrit and Oxyhemoglobin Saturation," Am J Circ Physiol 253: H147-H153 (1987).

Suarez et al., "Sudden Cardiac Death in Diabetes Mellitus: Risk Factors In The Rochester Diabetic Neuropathy Study," J. Neurol. Neurosurg. Psychiatry 76:240-245 (2005).

Tatersall et al., "Unexplained Deaths of Type 1 Diabetic Patients," Diabetic Medicine 8:49-58 (1990).

Zipes et al., "Sudden Cardiac Death", Circulation 98:2334-2351 (1998).

Zipes et al., "ACC/AHA/ESC Practice Guidelines," Circulation e392 (2006).

* cited by examiner

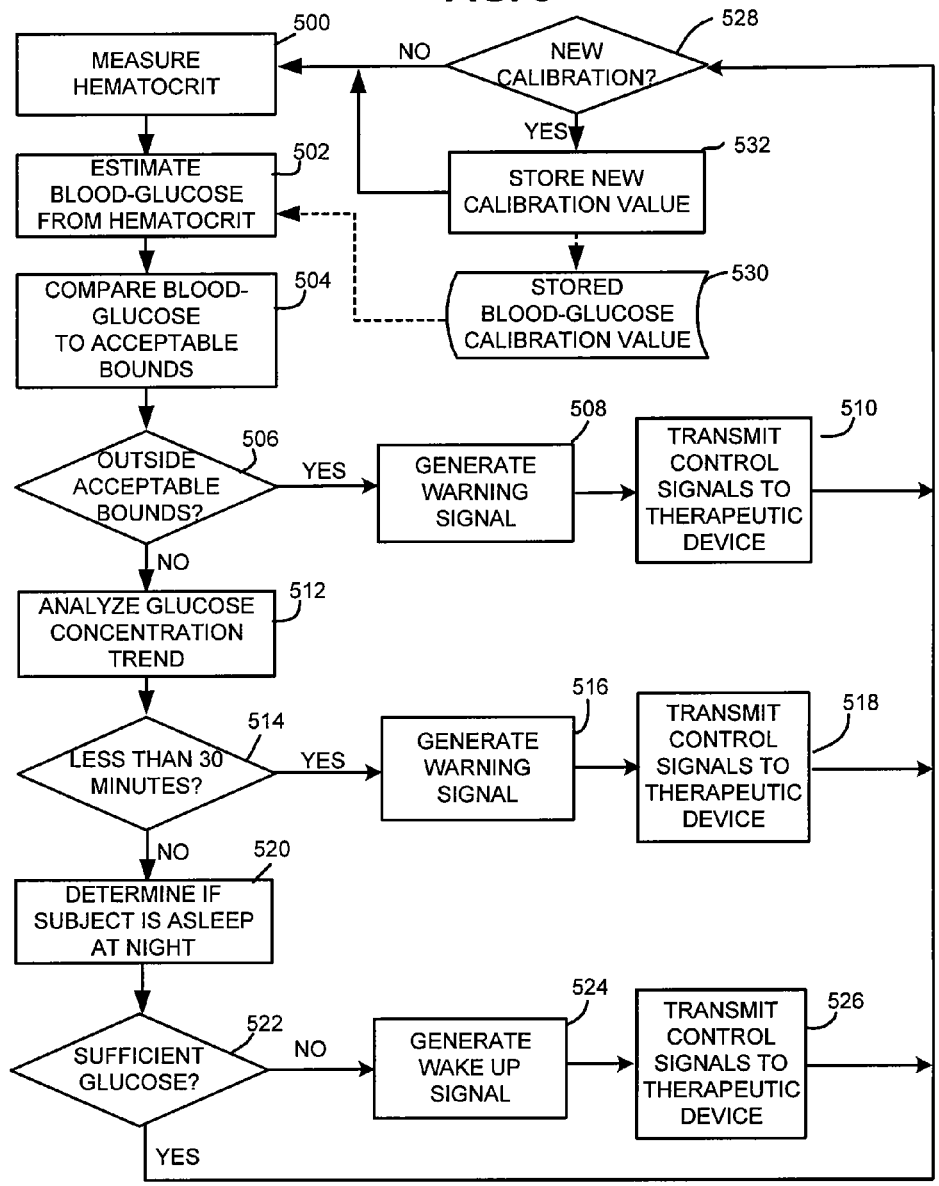

IMPLANTABLE CARDIAC DEVICE AND METHOD FOR MONITORING BLOOD-GLUCOSE CONCENTRATION

FIELD OF THE INVENTION

Embodiments of the present invention relate to implantable systems and methods for monitoring blood-glucose concentration and blood-glucose concentration trends by measuring hematocrit. The blood-glucose concentration and trend information is used to reduce the incidence of adverse consequences of cardiac disease and diabetes.

BACKGROUND OF INVENTION

Cardiac disease has high comorbidity with diabetes. Up to 45% of individuals with bradycardia or tachycardia also suffer from diabetes. Diabetes is a life-long disease marked by high concentrations of glucose in the blood. The sugar called glucose enters the bloodstream when food is digested. Glucose is a source of fuel for the body. In response to the glucose in the bloodstream, an organ called the pancreas makes the hormone insulin. The role of insulin is to move glucose from the bloodstream into muscle, fat, and liver cells, where it can be used as fuel. Individuals with diabetes either do not produce insulin (Type I diabetes) or are resistant to insulin (Type II diabetes). Consequently, the concentration of glucose in the blood in a person with diabetes may vary by a large amount dependent upon what they have eaten and the person's metabolic requirements. Variation in blood-glucose concentration can cause adverse consequences for diabetics and individuals with cardiac disease.

Studies have suggested that hypoglycemia (abnormally low blood-glucose) may precipitate transient atrial fibrillation, arrhythmia and tachycardia. Collier et al., "Transient Atrial Fibrillation Precipitated By Hypoglycaemia: Two Case Reports," Postgraduate Medical journal 63, 895-897 (1987); Shimada et al., "Arrhythmia During Insulin-Induced Hypoglycemia in a Diabetic Patient," Arch. Intern. Med. 144, 1068-9 (1984). It has been suggested that hypoglycemia-induced arrhythmia is a possible cause of sudden death during the sleep. Tattersall et al., "Unexplained Deaths of Type 1 Diabetic Patients," Diabetic Med. 8(1):49-58 (1991). Moreover some studies show that although implanted defibrillators can cause a significant reduction in mortality in high-risk cardiac disease patients they have less impact on the rate of sudden death in sleeping patients with cardiac disease "dead-in-bed." It is suggested that such deaths are the result of untreated hypoglycemia and consequent arrhythmia resulting. Moreover, when hypoglycemia is present, resultant arrhythmia may be resistant to treatment by pacing. In one case study hypoglycemia-triggered supraventricular tachycardia and rendered an antitachycardia pacemaker ineffective until the blood-glucose concentration was increased. Rokas et al., "Proarrhythmic Effects of Reactive Hypoglycemia," Pace 15, 373-376 (1992).

Blood-glucose concentration control is essential to the prevention of hypoglycemia and its adverse cardiac consequences. Blood-glucose concentration monitoring is the first step in blood-glucose concentration control. Typically, a sample of blood must be drawn and then the blood-glucose concentration assayed using color changing strips or an electrical device. To ensure proper dosage of insulin, individuals with diabetes use lancets to draw blood for conventional glucose measurements. A disadvantage of current blood-glucose concentration testing is that the painful process of drawing blood limits the number of times an individual is willing to take measurements. Even where external blood-glucose concentration monitoring does not require blood samples, it is still a disadvantage that the process requires active user intervention. Patients may forget to measure their blood-glucose concentration regularly and are not able to monitor their own blood-glucose concentration while sleeping.

In view of the many disadvantages of conventional external blood-glucose concentration monitoring techniques, implantable blood-glucose concentration monitors have been investigated. Such monitors typically require sensors for mounting directly within the blood stream. Most implantable glucose sensors that have been proposed are amperometric enzymatic biosensors which use immobilized glucose oxidase, an enzyme that catalyzes the oxidation of glucose to gluconic acid with the production of hydrogen peroxide. However, such amperometric enzymatic biosensors tend to clog very quickly. Thus, despite the demand for such a sensor, no implantable blood-glucose concentration sensor has yet achieved widespread use.

In view of the disadvantages of the state of the art with respect to blood-glucose monitors, it would be desirable to have a system that could painlessly measure blood-glucose concentration without drawing blood each time.

It would also be desirable to have a system that would automatically measure blood-glucose concentration of a patient without active user intervention.

It would further be desirable to have an implantable system that could measure glucose concentration without amperometric enzymatic biosensors.

SUMMARY OF INVENTION

In view of the background above and disadvantages of the state of the art, the present invention provides, in one embodiment, an implantable medical device which monitors blood-glucose concentration without the use of an amperometric enzymatic biosensor. The implantable medical device uses a sensor to monitor changes in hematocrit and determine changes in blood-glucose concentration based upon the changes in hematocrit. In accordance with one embodiment, the implantable medical device compares the blood-glucose concentration against upper and lower acceptable bounds and generates warning signals when the concentration falls outside the acceptable bounds. In one example, in which an implantable insulin pump and/or glucose pump is provided, the delivery of insulin and/or glucose is regulated in response to the calculated blood-glucose concentration to maintain blood-glucose concentration within an acceptable range and guard against hyperglycemia, hypoglycemia and hypoglycemia-induced arrhythmia.

In specific embodiments, the implantable medical device is an implantable cardiac device ("ICD") such as a pacemaker, defibrillator or other implantable cardiac stimulation device. Blood-glucose concentration monitoring is conveniently provided within patients already requiring an ICD, without requiring implantation of additional devices. This combination is particularly useful because of the high comorbidity of diabetes and heart disease. Moreover, the blood-glucose concentration and/or changes therein can be calculated as often as needed without patient intervention. For example, the blood-glucose concentration may be monitored while the patient is sleeping to reduce the risk of hypoglycemia. Once the blood-glucose concentration has been calculated, the pacemaker or ICD compares the blood-glucose concentration against acceptable upper and lower bounds and generates appropriate warning signals if the concentration is outside the acceptable bounds. If an implantable insulin pump or other therapeutic device is provided, the insulin pump or other therapeutic device is automatically controlled in response to the calculated blood-glucose concentration to maintain the concentration within an acceptable range. Thus, the ICD of an embodiment of the present invention can reduce the incidence of hypoglycemia-induced arrhythmia and also treat hypoglycemia-induced arrhythmia that is resistant to pacing.

In a specific embodiment, an ICD is provided with an implantable oxymetry sensor which is used to measure hematocrit and can also be used to measure oxygen saturation. The pacemaker or ICD is provided with a control unit which utilizes the hematocrit and the relationship between hematocrit and blood-glucose concentration to calculate blood-glucose concentration from hematocrit measurements. In accordance with a further aspect of the invention, a calibration technique is provided for use in determining blood-glucose concentration. The calibration technique can be implemented using an external blood-glucose monitor in communication with the ICD. The external blood-glucose monitor measures blood-glucose concentration using otherwise conventional techniques, such as the hexokinase method, and transmits the blood-glucose concentration to the pacemaker or ICD. The ICD calculates the blood-glucose concentration at a later time from the externally measured blood-glucose concentration and measurement of changes in hematocrit.

Thus, various techniques are provided for monitoring blood-glucose concentration based on hematocrit and for calibrating an implantable medical device such as an ICD for use with individual patients. The monitoring and control of glucose concentration facilitated by the invention is beneficial to individuals with cardiac disease and diabetics as well as subjects who have not been diagnosed as diabetic. The amelioration of hypoglycemia reduces the risk and incidence of adverse effects of diabetes and cardiac disease. Other alternatives, objects, features and advantages of the invention will be apparent from the detailed description which follows.

BRIEF DESCRIPTION OF THE DRAWINGS

The above and further features, advantages and benefits of the present invention will be apparent upon consideration of the present description taken in conjunction with the accompanying drawings.

FIG. 5 is a flow diagram illustrating a method performed by the blood-glucose analysis unit of FIG. 2 to calculate blood-glucose concentration in accordance with specific embodiments of the present invention.

DETAILED DESCRIPTION

Figure 1:
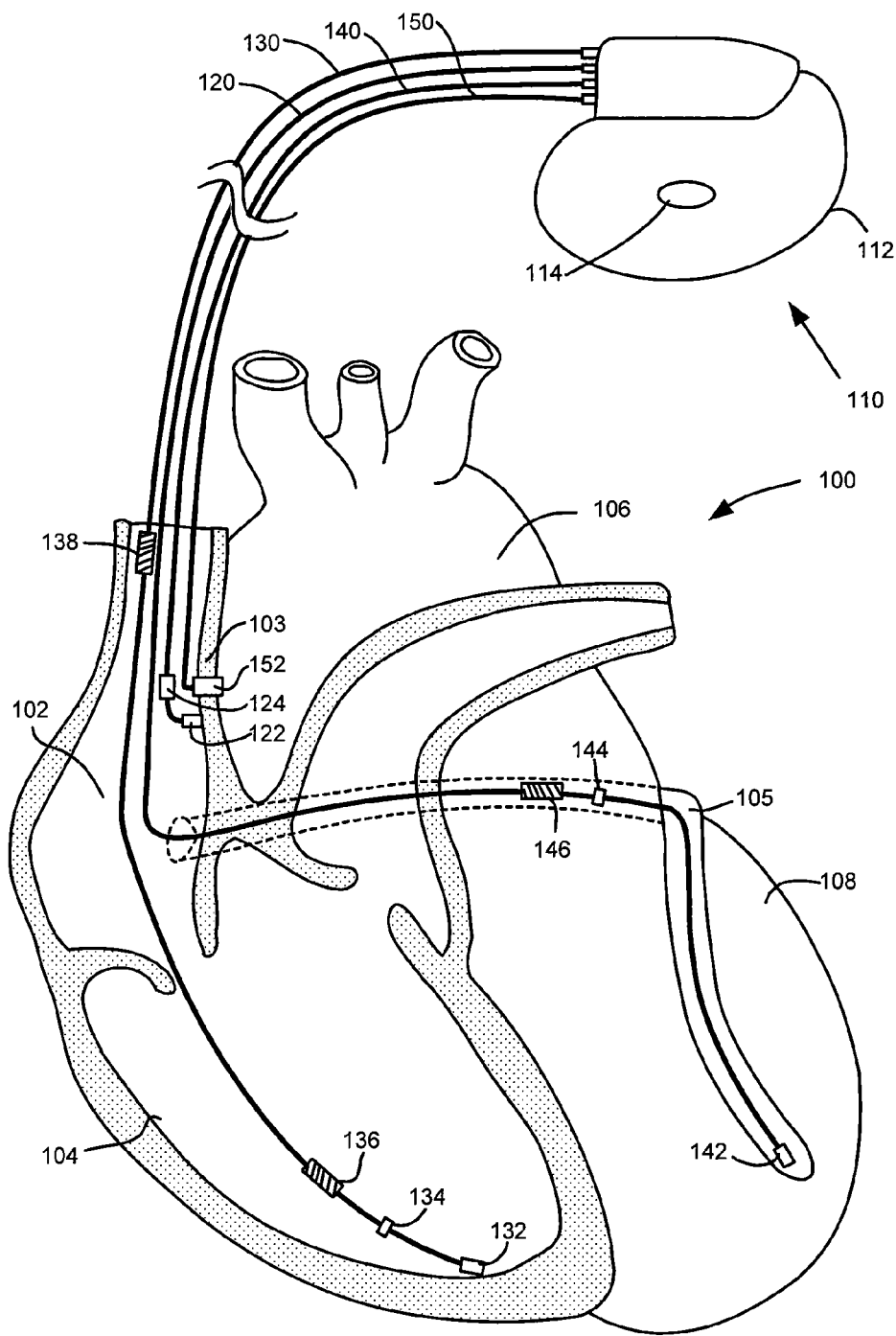
FIG. 1 is a simplified, partly cutaway view illustrating an ICD in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the left-most digit of a reference number identifies the drawing in which the reference number first appears.

ICD

FIG. 1 illustrates an exemplary ICD 110 in electrical communication with a patient's heart 100 by way of four leads 120, 130, 140 and 150 suitable for multi-chamber sensing, stimulation and shock therapy. To sense atrial cardiac signals and to provide right atrial chamber stimulation therapy, ICD 110 is coupled to an implantable right atrial lead 120 having at least an atrial tip electrode 122, which typically is implanted in the patient's right atrial appendage. In accordance with one embodiment of the present invention, right atrial lead 120 also comprises an oxymetry sensor 124 for measuring hematocrit and mixed-venous oxygen saturation. Alternatively, or in addition a PPG sensor 114 capable of measuring hematocrit may be integrated into housing 112 of ICD 110. Utilizing hematocrit measurements from oxymetry sensor 124 or PPG sensor 114, ICD 110 is capable of continuously monitoring blood-glucose concentration and blood-glucose concentration trends using the methods described below.

To sense left atrial and ventricular cardiac signals and to provide left-chamber pacing therapy, ICD 110 is coupled to a "coronary sinus" lead 140 designed for placement in the "coronary sinus region" 105 via the coronary sinus so as to place a distal electrode adjacent to the left ventricle 108 and additional electrode(s) adjacent to the left atrium 106. As used herein, the phrase "coronary sinus region" 105 refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 140 is designed to receive atrial and ventricular cardiac signals and to deliver left ventricular pacing therapy using at least a left ventricular tip electrode 142, left atrial pacing therapy using at least a left atrial ring electrode 144, and shocking therapy using at least a left atrial coil electrode 146.

ICD 110 is also shown in communication with the patient's heart 100 by way of an implantable left atrial lead 150 having in this embodiment, a left atrial sensor 152 implanted in the septum 103 between the right atrium 102 and left atrium 106. A suitable embodiment of a lead-mounted left atrial sensor is the Savacor HEARTPOD™ which in the present application is connected via lead 150 to ICD 110. Details of such left atrial sensor modules may be found in U.S. patent application Ser. No. 11/115,991 entitled, "Implantable Pressure Transducer System Optimized For Anchoring And Positioning" filed Apr. 27, 2005 to Eigler et al.; Ser. No. 10/270,784 entitled "Permanently Implantable System And Method For Detecting, Diagnosing And Treating Congestive Heart Failure" filed: Oct. 11, 2002 to Eigler et al.; and Ser. No. 11/027,598 entitled "Flexible Lead For Digital Cardiac Rhythm Management" filed: Dec. 30, 2004 to Mann et al., all of which are incorporated herein by reference.

ICD 110 is also shown in electrical communication with the patient's heart 100 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 100 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle.

Figure 2:
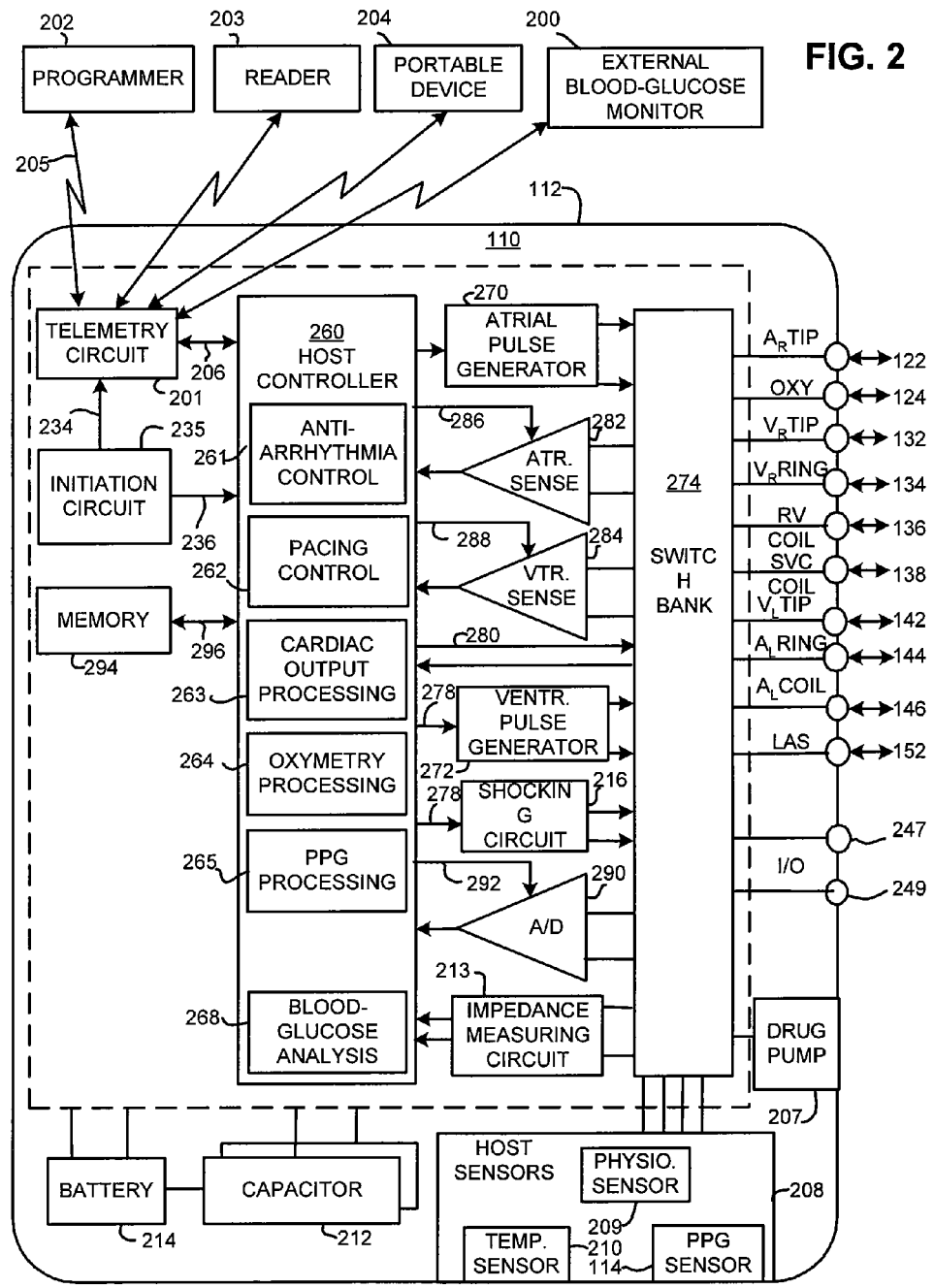
FIG. 2 is a functional block diagram of the multi-chamber ICD of FIG. 1, illustrating the basic elements that provide cardioversion, defibrillation and/or pacing stimulation in four chambers of the heart and illustrating a blood-glucose concentration monitoring unit for automatically determining blood-glucose concentration in accordance with specific embodiments of the present invention.

FIG. 2 illustrates a simplified block diagram of the multi-chamber ICD 110 which is capable of determining blood-glucose concentration from measurements of hematocrit, using the calculated blood-glucose concentration for diagnostic or therapeutic purposes, and treating both fast and slow arrhythmias with stimulation therapy, including cardioversion, defibrillation, and pacing stimulation. While a particular multi-chamber device is shown, this is for illustrative purposes only and one of skill in the art could readily duplicate, eliminate or disable the appropriate circuitry in any desired combination to provide a device capable of determining blood-glucose concentration in accordance with the present invention with or without treating the heart with cardioversion, defibrillation and/or pacing stimulation.

Referring again to FIG. 2, ICD 110 includes a housing 112 which is often referred to as a "can", "case" or "case electrode", and which may be programmably selected to act as the return electrode for all "unipolar" modes. Housing 112 may further be used as a return electrode alone or in combination with one or more of the coil electrodes 146, 136, or 138, for shocking purposes. Housing 112 further includes a connector (not shown) having a plurality of terminals, 242, 243, 244, 245, 246, 247, 248, 249, 252, 254, 256, and 258 (shown schematically and, for convenience, the names of the electrodes to which they are connected are shown next to the terminals). To achieve right atrial sensing and pacing, the connector includes at least a right atrial tip terminal 242 adapted for connection to the right atrial (AR) tip electrode 122, a right atrial oxymetry sensor terminal 243 adapted for connection to the oxymetry sensor 124. To achieve left chamber sensing, pacing and/or shocking, the connector includes at least a left ventricular (VL) tip terminal 244, a left atrial sensor terminal, 245, a left atrial (AL) ring terminal 246, and a left atrial (AL) shocking terminal (coil) 248, which are adapted for connection to the left ventricular tip electrode 142, the left atrial ring electrode 144, and the left atrial coil electrode 146, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively. The connector may also include one or more I/O terminals 247, 249 for communicating with optional implantable devices external to housing 112.

At the core of ICD 110 is a programmable host controller 260 which controls the various modes of stimulation therapy and performs calculations of blood-glucose concentration using the methods of the present invention. As is well known in the art, host controller 260 may be a microcontroller and typically includes a microprocessor or equivalent control circuitry or processor, designed specifically for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. Host controller 260 includes the ability to calculate blood-glucose concentration from measured oxymetric, temperature, and electrocardiographic variables and stored parameters. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by right atrial lead 120, right ventricular lead 130, and/or coronary sinus lead 140 via a switch bank 274. It is understood that in order to provide stimulation therapy in each of the four chambers of the heart, atrial pulse generator 270 and ventricular pulse generator 272 may include dedicated, independent pulse generators, multiplexed pulse generators, or shared pulse generators. Atrial pulse generator 270 and ventricular pulse generator 272 are controlled by host controller 260 via appropriate control signals 276 and 278, respectively, to trigger or inhibit the stimulation pulses.

Host controller 260 further includes pacing control circuitry 262 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

ICD 110 may operate as an implantable cardioverter/defibrillator (ICD) device. That is, it may detect the occurrence of an arrhythmia, and automatically apply an appropriate electrical shock therapy to the heart aimed at terminating the detected arrhythmia. To this end, host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by the host controller 260. Such shocking pulses are applied to the patient's heart through at least two shocking electrodes, as shown in this embodiment, selected from left atrial coil electrode 146, RV coil electrode 136, and/or SVC coil electrode 138 (FIG. 1). As noted above, housing 112 may act as an active electrode in combination with the RV electrode 136, or as part of a split electrical vector using SVC coil electrode 138 or left atrial coil electrode 146 (e.g., using the RV electrode as a common electrode).

Switch bank 274 includes a plurality of electrically-configurable switches for connecting the desired electrodes to the appropriate I/O circuits, thereby providing complete electrode programmability. Accordingly, switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave.

Atrial sensing circuits 282 and ventricular sensing circuits 284 may also be selectively coupled to right atrial lead 120, coronary sinus lead 140, and right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. Switch bank 274 determines the "sensing polarity" of the cardiac signal by selectively closing the appropriate switches. In this way, the clinician may program the sensing polarity independent of the stimulation polarity.

Each of the sensing circuits, 282 and 284, preferably employ one or more low power, precision amplifiers with programmable gain and/or automatic gain control, bandpass filtering, and a threshold detection circuit, to selectively sense the cardiac signal of interest. The automatic gain control enables ICD 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

For arrhythmia detection, ICD 110 utilizes the atrial and ventricular sensing circuits 282 and 284 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition unit 290. Data acquisition unit 290 is configured to acquire intracardiac electrogram signals, convert the raw analog data into digital signals, and store the digital signals for later processing and/or telemetric transmission to an external device such as programmer 202, reader 203 or portable device 204. Data acquisition unit 290 is coupled to right atrial lead 120, the coronary sinus lead 140, the right ventricular lead 130, and the left atrial lead 150 through the switch bank 274 to sample cardiac signals across any pair of desired electrodes.

Advantageously, data acquisition unit 290 may be coupled to host controller 260 or other detection circuitry, for detecting an evoked response from the heart 100 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition unit 290 via control signal 292 to sample the cardiac signal that falls in the capture detection window and, based on the amplitude of the sampled cardiac signal, determines if capture has occurred. The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection unit used is not critical to the present invention.

ICD 110 may also include one or more host sensors 208, which can be located within the housing 112 of ICD 110 as shown, or can be located external to the housing. These sensors can include, by way of example, blood flow sensors, temperature sensors, and blood pressure sensors. Host sensors 208 may include a physiologic sensor 209, a temperature sensor 210 and PPG sensor 114. As shown in FIG. 2, host sensors 208 may be connected via switch bank 274 to host controller 260 directly or through data acquisition unit 290 such that host controller 260 can receive measurements of the physiological variables from the host sensors 208.

Physiologic sensor 209 is commonly referred to as a "rate-responsive" sensor because it is typically used to adjust pacing stimulation rate according to the exercise state of the patient. However, the rate-responsive sensor may also be used to detect changes in cardiac output, changes in the physiological condition of the heart, or diurnal changes in activity (e.g., detecting sleep and wake states). Accordingly, host controller 260 responds to the rate-responsive sensor by adjusting the various pacing parameters (such as rate, AV Delay, V-V Delay, etc.) at which the atrial and ventricular pulse generators, 270 and 272, generate stimulation pulses.

As further shown in FIG. 2, ICD 110 comprises an impedance measuring circuit 213 which is enabled by host controller 260 via a control signal 214. Certain applications for an impedance measuring circuit 213 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. Impedance measuring circuit 213 is advantageously coupled to the switch bank 274 so that any desired electrode may be used for impedance measurement.

Host controller 260 is also coupled to a memory 294 by a suitable data/address bus 296. Memory 294 stores the programmable operating parameters used by the host controller 260 in order to customize the operation of ICD 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 100 within each respective tier of therapy. A feature of ICD 110 is the ability to receive and store a relatively large amount of data (e.g., from data acquisition unit 290), which data may then be used for subsequent analysis to guide the programming of ICD 110.

Advantageously, the operating parameters of the ICD 110 may be non-invasively programmed into the memory 294 through a telemetry circuit 201 in telemetric communication with an external programmer 202, such as a, transtelephonic transceiver, or a diagnostic system analyzer. The telemetry circuit 201 is activated by the host controller by a control signal 206. The telemetry circuit 201 advantageously allows intracardiac electrograms, blood-glucose concentration results, oxygen saturation information, temperature data, hematocrit information, stroke volume, heart-rate, other measured physiological variable and status information relating to the operation of the ICD 110 (as contained in the host controller 260 or memory 294) to be sent to or received from an external device such as programmer 202, reader 203, portable device 204, or external glucose monitor 200 through an established communication link 205. Typically the communication link can only operate between telemetry circuit 201 and one of programmer 202, reader 203, portable device 204 or external glucose monitor 200 at any one time. A "handshake" signal sent from the external device may be used to identify the particular device with which the telemetry circuit 201 is in communication thereby defining what operations may be performed by the device. For example, programming of ICD 110 will preferably only be permitted by programmer 202 under the control of a physician.

ICD 110 further includes initiation circuit 235. Initiation circuit 235 may comprise magnet detection circuitry. Initiation circuit 235 is coupled to host controller 260 by connection 236 and/or to telemetry circuit 201 by connection 234. The purpose of the initiation circuit is to detect an initiation signal from outside the patient. For example, a magnet placed over the cardiac ICD 110 may be used as the initiation signal, which magnet may be used by a clinician to perform various test functions of the cardiac ICD 110 and/or to signal host controller 260 that an external programmer 202 is in place to receive or transmit data to host controller 260 through the telemetry circuit 201. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (note: this relates to transfer of EGM data) (McClure et al.), which patents are hereby incorporated herein by reference.

ICD 110 additionally includes a power source such as a battery 214 which provides operating power to all the circuits of ICD 110. For ICD 110, which employs shocking therapy, battery 214 must be capable of operating at low current drains for long periods of time and also be capable of providing high-current pulses (for charging capacitor 212) when the patient requires a shock pulse. Battery 214 preferably has a predictable discharge characteristic so that elective replacement time can be detected. Accordingly, ICD 110 can employ lithium/silver vanadium oxide batteries.

A photoplethysmography (PPG) sensor 114 can be used to measure blood hematocrit and oxygen saturation in the tissues adjacent the housing 112. PPG Sensor 114 may be provided in addition to or instead of oxymetry sensor 124 to measure hematocrit in accordance with a specific embodiment of the present invention. PPG Sensor 114 comprises multiple light sources of different wavelengths of light and at least one light sensor. The light sensor measures the intensity of light from the light sources which is reflected back from the tissues next to PPG sensor 114. PPG sensor 114 provides light intensity measurements to PPG processing unit 265 of host controller 260. PPG processing unit 265 calculates hematocrit and arterial oxygen saturation from the light intensity measurements using standard oxymetry techniques. In an embodiment of the invention, oxymetry processing unit 264 calculates oxygen saturation and hematocrit information from the outputs of oxymetry sensor 124 (See FIG. 1). The calculation of oxygen saturation is not necessary to the operation of the present invention but provides useful metabolic information to the ICD 110.

Blood-glucose analysis unit 268 (also referred to as blood-glucose monitor 268) determines blood-glucose concentration trends and the current blood-glucose concentration within the bloodstream of the patient using the hematocrit measurements provided by oxymetry processing unit 264 or PPG processing unit 265. In addition blood-glucose analysis unit 268 may receive blood-glucose calibration values from an external blood-glucose monitor 200 or another blood-glucose monitor. The blood-glucose calibration values and/or calculated blood-glucose concentration values may optionally be stored in memory 294. The operation of blood-glucose analysis unit 268 is described in detail below with reference to FIGS. 4A, 4B and 5.

An effector may be provided to provide therapeutic treatment to control blood-glucose concentration in response to measurement of blood-glucose concentration. For example, if a drug pump 207 is provided, blood-glucose analysis unit 268 transmits control signals to drug pump 207 for adjusting the amount of a therapeutic agent delivered to the patient in response to the current blood-glucose concentration. The therapeutic agent may be an agent that decreases blood-glucose concentration—such as insulin—or an agent that increases blood-glucose concentration such as glucose or glucagon. Information regarding implantable pumps may be found in U.S. Pat. No. 4,731,051 to Fischell and in U.S. Pat. No. 4,947,845 to Davis, both of which are incorporated by reference herein. The insulin pumps discussed therein, or other suitable insulin pumps, are modified as needed to permit receipt of control signals from blood-glucose analysis unit 268. Blood-glucose analysis unit 268 can likewise be used to control other implantable therapeutic devices which can be used to affect blood-glucose concentration. For example, it has been suggested that stimulation of the autonomic nerves innervating the pancreas may be used to control insulin secretion. This stimulation could be achieved using properly placed electrodes connected to terminals of ICD 110. The stimulation may be adjusted in response to control signals from blood-glucose analysis unit 268 thereby affecting the amount of insulin and/or glucagon secreted by the pancreas in response to the calculated blood-glucose level.

Glucose Concentration Calculation Using Hematocrit

As, described in the background of the invention, it is desirable to provide for automatic monitoring of blood-glucose in an implantable medical device, such as in an ICD as described above. However currently available methods and sensors for monitoring blood-glucose suffer from numerous disadvantages. In order to overcome the disadvantages of the state of the art, techniques for monitoring blood-glucose concentration using measurements of hematocrit are provided herein. Hematocrit may be readily measured using sensors including, but not limited to, spectroscopic sensors such as oxymetry and PPG sensors.

Hematocrit is affected by the osmolarity of the blood plasma. Osmolarity of the blood plasma is mainly a function of the concentration of sodium and its anions (mainly chloride and carbonate ions) with additional contributions from glucose and urea. However, urea readily crosses cell membranes and therefore equilibrates between the cells and plasma. Thus, the effective osmolarity of the blood is dependent principally on the concentration of sodium ions (and associated cations) and glucose in the plasma. the following formula can be used to express the effective Osmolarity of blood:

$$\text{Osmolarity (mOsm/L H}_2\text{O)} = 2*[\text{Na}^+(\text{mEq/L})] + [\text{Glucose (mg/dl)}]/18$$

In normal patients, the sodium ion concentration is 142 mEq/L and the glucose concentration is 90 mg/dl. However, in diabetics the blood-glucose concentration may vary over a wide range and can cause approximately 10% variation in the osmolarity of the blood.

The cells and interstitial fluid contain many different solutes such as electrolytes, proteins, glucose and metabolic products. Some of these solutes can pass through cellular membranes and some cannot. When the osmolarity of the blood changes, the water passes in or out of the blood vessels to balance the osmotic pressure difference between the cells, the interstitial fluid and the blood plasma. Thus, the volume of the blood changes as a result of changes in its osmolarity. When the volume of the blood changes, the hematocrit (the volume percent of blood cells in the blood) also changes. This change in hematocrit resulting from the change in blood-glucose concentration can be measured in accordance with the present invention.

Figure 3A:
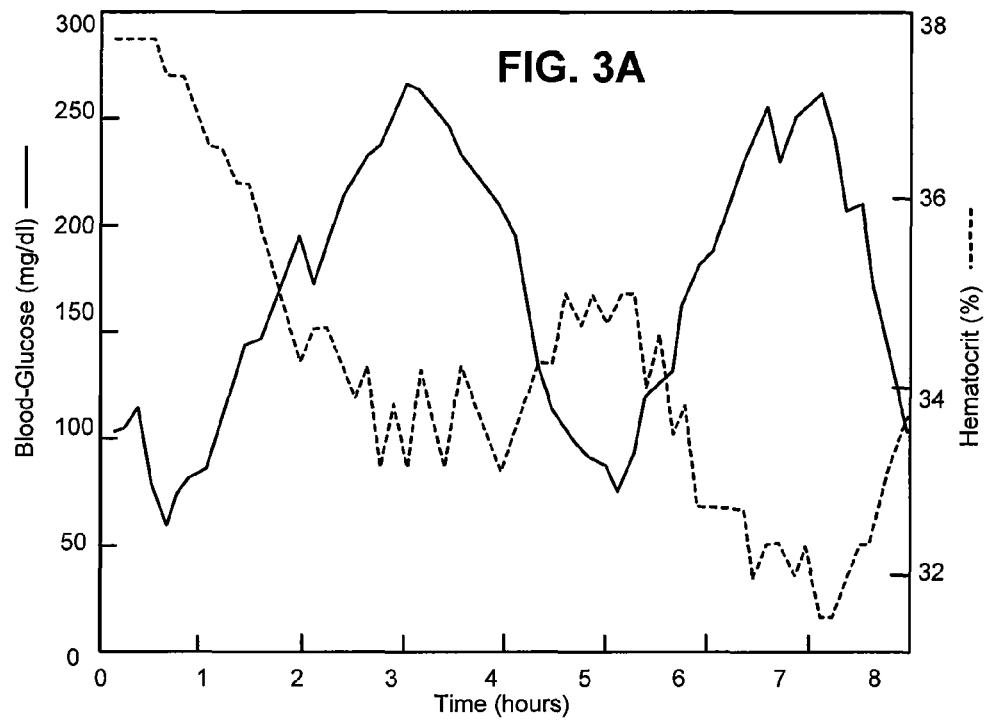
FIG. 3A and FIG. 3B are charts showing the results of an experiment relating variation of hematocrit with glucose concentration.
Figure 3B:
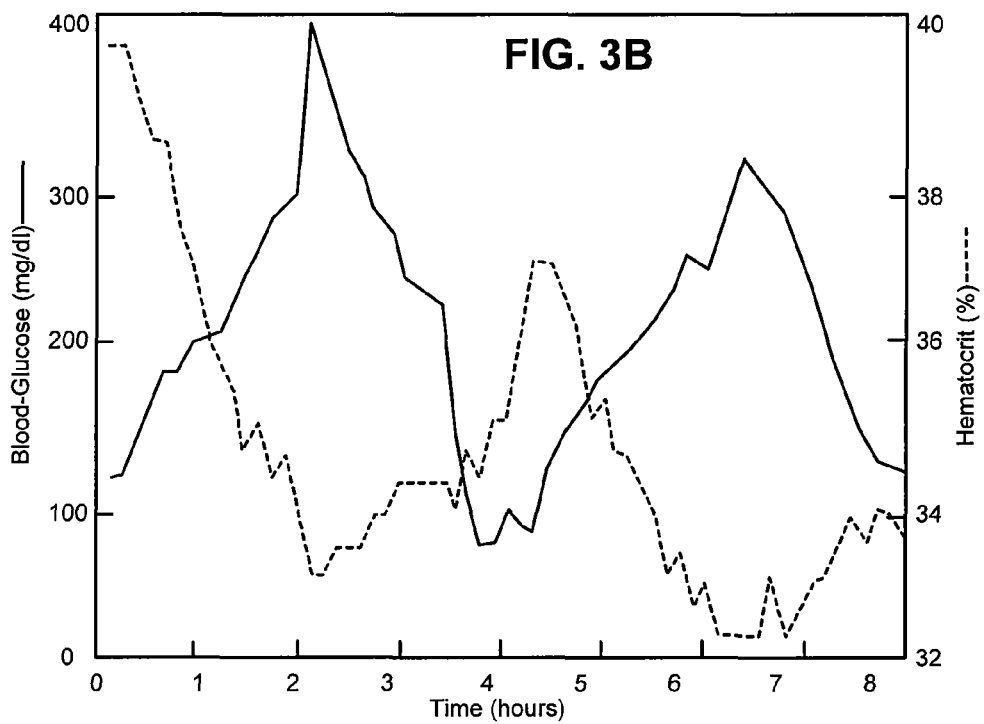

FIGS. 3A and B are charts showing the results of an experiment in which the hematocrit and blood-glucose concentration of an experimental subject were measured over an eight hour period. The solid lines indicate the change in blood-glucose concentration over an eight hour period and the dashed lines indicate the corresponding change in hematocrit over the same eight hour period. As can be seen from the experimental data, when blood-glucose concentration increases, the hematocrit decreases. The increased blood-glucose concentration increases the osmolarity of the blood. The increased osmolarity of the blood causes water to leave the cells of body and interstitial fluid and enter the blood plasma. This shift in water causes the total volume of the blood to increase. Since the number of blood cells does not change, the hematocrit decreases. Likewise when blood-glucose concentration decreases, the blood volume decreases and hematocrit increases. It is apparent from the experimental data of FIGS. 3A and 3B that there is a measurable inverse correlation between hematocrit and blood-glucose concentration.

In accordance with specific embodiments of the present invention, blood-glucose concentration and blood-glucose concentration trends are estimated using a formula which relates blood-glucose concentration to hematocrit. In a simple example correlating the experimental results for hematocrit and glucose concentration shown in FIG. 3A the blood-glucose concentration can be predicted from hematocrit as follows:

$$[\text{Glucose (mg/dl)}] = 1300 - 33*\text{Hct}(\%)$$

The blood-glucose concentration estimated from measurements of hematocrit matches well with the actual glucose concentration. Likewise the rate of change in glucose concentration can be estimated from the rate of change in hematocrit as follows:

$$[\Delta\text{Glucose (mg/dl hr)}] = -33*\Delta\text{Hct}(\%/\text{hr}).$$

Thus, the blood-glucose concentration and the rate of change of blood-glucose concentration can be readily estimated from measurements of hematocrit in accordance with embodiments of the present invention. The blood-glucose concentration can thus be periodically, aperiodically or continuously monitored by the implantable medical device without user intervention and without the need for a conventional implantable glucose sensor. Exemplary, implantable devices and ICD's which use the blood-glucose concentration estimates and trends for diagnostic and therapeutic purposes are described in more detail herein.

External Blood-Glucose Monitor

For certain applications it is desirable to ascertain actual blood-glucose concentration values in addition to changes or trends in blood-glucose concentration. In order to determine actual blood-glucose concentrations it is preferable to measure blood-glucose concentration from time to time using a method other than the hematocrit method described above. In one embodiment of the present invention a direct measurement of blood-glucose is made from time to time to determine a blood-glucose calibration value. In a preferred embodiment the blood-glucose calibration value is determined at least once per day. In one embodiment of the present invention, an external blood-glucose monitor is used to generate the blood-glucose calibration value. The ICD utilizes hematocrit measurements to provide continuous estimates of blood-glucose concentration between uses of the external blood-glucose monitor.

A wide range of external blood-glucose monitors are known in the art. Some external blood-glucose sensors require the patient to obtain and test a blood sample. Other external blood-glucose monitors are non-invasive. For the purposes of the present invention, any blood-glucose monitor may be used so long as the actual blood-glucose concentration is transmitted to the implantable medical device at about the same time as it is measured. In some cases, the external blood-glucose monitor 200 is provided with circuitry for transmitting the blood-glucose calibration value to the ICD 110 as illustrated in FIG. 2. In an alternative embodiment, the external blood-glucose calibration value may be measured and displayed by the external blood-glucose monitor and a user may enter the blood-glucose calibration value into a device that can transmit the information to the ICD such as programmer 202 or portable device 204. In an alternative embodiment, the external blood-glucose calibration value may be measured and displayed by the external blood-glucose monitor and automatically transmitted via a wireless or wired link into a device that can transmit the information to the ICD such as programmer 202 or portable device 204. Thus, the ICD 110 may obtain the blood-glucose calibration value in a number of alternative ways.

Figure 4A:
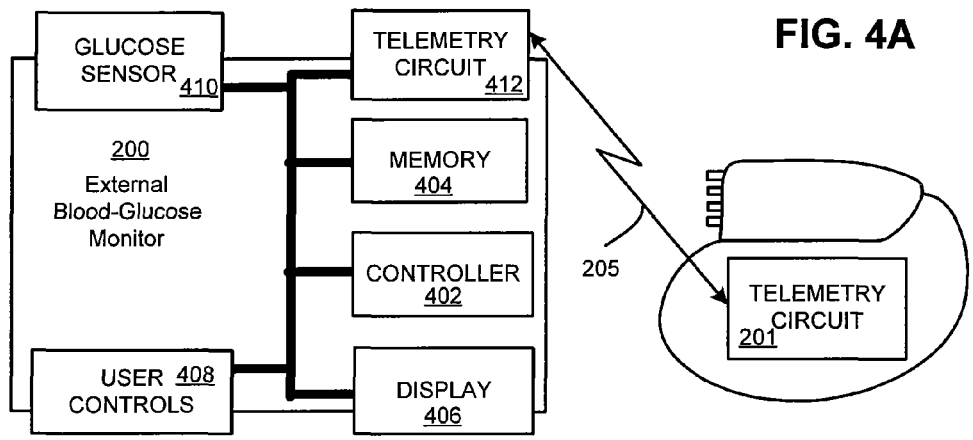
FIG. 4A is functional block diagram illustrating components of an external blood-glucose monitor for use with the blood-glucose concentration monitoring unit of an implantable medical device in accordance with specific embodiments of the present invention.

FIG. 4A illustrates exemplary components of external blood-glucose monitor 200 suitable for use with an ICD 110 for determining blood-glucose concentration in accordance with an embodiment of the present invention. External blood-glucose monitor 200 permits a user to measure blood-glucose concentration and transmit a blood-glucose calibration value to ICD 110. Operations of external blood-glucose monitor 200 are controlled by a controller 402, which may be a generally programmable microprocessor or microcontroller or may be a dedicated processing device such as an application specific integrated circuit (ASIC) or the like. Software instructions to be performed by the controller are accessed from a memory 404 which may be a read only memory, random access memory or flash memory. Controller 402 displays a menu of options to the user via a suitable display device 406. To this end, controller 402 may, for example, display a menu of actions to be performed on display device 406. In response thereto, the patient enters various commands via user controls 408 which may comprise buttons or a touch screen or other type of user input device.

The patient, or another user, initially controls external blood-glucose monitor 200 to measure the patient's blood-glucose concentration. Controller 402 measures the patient's blood-glucose concentration using glucose sensor 410. Glucose sensor 410 may comprise any conventional external blood-glucose sensor which monitors the concentration of glucose in samples of the patient's blood using standard methods such as the hexokinase method. Controller 402 receives the blood-glucose concentration from blood-glucose sensor 410 and stores the blood-glucose value in memory 404. Controller 402 optionally displays the blood-glucose concentration to the patient on display 406. Controller 402 then transmits the blood-glucose calibration value to the ICD 110. The data may be transmitted automatically as soon as it is measured or controller 402 may wait for user input prior to transmission. The blood-glucose calibration value is transmitted to ICD 110 by telemetry circuit 412 over a telemetry link 205.

Figure 4B:
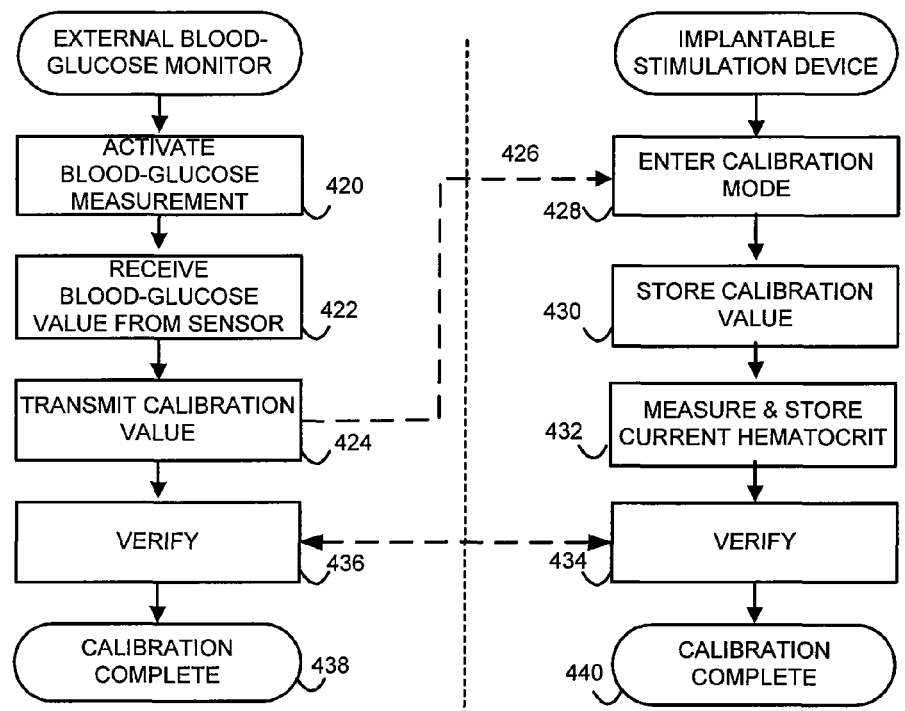
FIG. 4B is a flowchart illustrating a calibration technique performed by both the ICD of FIG. 2 and the external blood-glucose monitor of FIG. 3 in accordance with specific embodiments of the present invention.

In FIGS. 4B and 5, flow charts are provided illustrating the operation and novel features of various exemplary embodiments of the invention. In the flow charts, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

FIG. 4B is a flowchart illustrating steps performed by the ICD 110 in cooperation with the external blood-glucose monitor 200 of FIG. 4A in accordance with specific embodiments of the present invention. At step 420, on instructions from the user, external blood-glucose monitor 200 is activated for blood-glucose measurement. At step 422, blood-glucose sensor 410 determines the current blood-glucose concentration of the patient. At step 424, external blood-glucose monitor 200 establishes a communication link with ICD 110 and transmits the blood-glucose calibration value. This step may be automatic after a blood-glucose measurement is made or it may wait for user instruction. At step 428, ICD 110 receives blood-glucose calibration value 426 and enters blood-glucose calibration mode. At step 430, ICD stores the blood-glucose calibration value. At step 432, ICD 110 measures and stores the current hematocrit of the patient which corresponds with the blood-glucose calibration value 426. At step 434, ICD 110 verifies the received blood-glucose calibration value to ensure that it is within the expected range of blood-glucose values and transmits a confirmation to external blood-glucose monitor 200. At step 436, external blood-glucose monitor 200 transmits a confirmation back to ICD 110. At step 438, external blood-glucose monitor displays a message to the user indicating that the blood-glucose calibration value has been correctly measured and transmitted to the ICD 110. At step 440, ICD 110 completes the blood-glucose calibration and leaves calibration mode. At this point ICD 110 may calculate actual blood-glucose concentration values by monitoring changes in hematocrit until a subsequent blood-glucose calibration event.

Referring now to FIG. 5, the operation of blood-glucose analysis unit 268 of FIG. 2 will be described. Hematocrit is measured at step 500. At step 502, blood-glucose analysis unit 268 estimates the blood-glucose concentration using the hematocrit and a prior measurement or estimation of blood-glucose concentration. At step 504, the blood-glucose estimate is compared to acceptable bounds for blood-glucose concentration. For example, the blood-glucose concentration estimate may be compared at step 504 against both an upper threshold and a lower threshold to ensure that the blood-glucose concentration is within acceptable bounds. In one example, the upper threshold is 120 mg/dl and the lower threshold is 60 mg/dl. The upper and lower threshold values are preprogrammed within the ICD 110 and may be specified, for example, by a physician using programmer 202. If the blood-glucose concentration is found to be outside the acceptable bounds at step 506, a warning signal is generated at step 508 to alert the patient. A drug pump 207 or other therapeutic device can also be adjusted at step 510, as described in more detail below.

At step 512, blood-glucose analysis unit 268 analyzes the blood-glucose concentration trend. The blood-glucose concentration trend can be calculated from the rate of change of hematocrit with or without a prior estimate of blood-glucose concentration. The rate of change of blood-glucose concentration is calculated and a time by which blood-glucose concentration will be out of bounds is calculated based on the current blood-glucose concentration and the rate of change. If the blood-glucose concentration is predicted to be outside the acceptable bounds within 30 minutes (or some other specified time) at step 514, an early warning signal is generated at step 516. A drug pump 207 or other therapeutic device can also be adjusted at step 518, as described in more detail below.

At step 520, it is determined whether the patient is asleep. This determination may be made by a separate calculation unit within controller 260 by methods familiar in the art e.g. using motion sensors, position sensors, respiratory sensors, breathing sensors, activity sensors and the like. It is beneficial to determine whether the patient is sleeping and estimate a projected time of waking in order to determine whether the patient will maintain adequate levels of glucose in the blood until waking. The anticipated length of the sleep may be determined by presets or derived from historical monitoring of the patients sleep habits. The sufficiency of glucose can be estimated from the blood-glucose concentration, the rate of change of blood-glucose concentration and the predicted length of sleeping. If the blood-glucose concentration is predicted to be outside the acceptable bounds before the patient wakes at step 522, a wake up or arousal signal is generated at step 524. A drug pump 207 or other therapeutic device can also be adjusted at step 526, as described in more detail below.

If a new calibration value for blood-glucose concentration is present at step 528, the blood-glucose calibration value 530 is stored at step 532. Steps 500-528 can be repeated at intervals to update the blood-glucose concentration measurement. For example, the measurement may be repeated once every minute, once every 15 minutes, or once every hour. Preferably, the interval between calculations of blood-glucose concentration is selected so as to maintain adequate control of blood-glucose concentration and programmed in advance by a physician using programmer 202. The interval between blood-glucose concentration measurement updates may also vary depending upon the glucose concentration, the rate of change of glucose concentration, or the activity of the patient. For example, if the rate of change of glucose concentration is determined to be high at step 512, the interval until the next update may be reduced compared to the normal update interval. Conversely, if the rate of change of glucose concentration is determined to be low at step 512, the interval until the next update may be increased compared to the normal update interval. Likewise, if the blood-glucose concentration is found to be below a threshold, such as 70 mg/dl or above a threshold such as 110 mg/dl the interval until the next update may be reduced compared to the normal update interval. The reduced interval between updates thus allows for more accurate analysis of the current blood-glucose level during high risk periods, i.e. when blood-glucose is changing rapidly or the patient is approaching hypoglycemia or hyperglycemia.

Preferably, a different warning signal is provided at step 508 when the blood-glucose concentration is too low than when it is too high. Additionally, the early warning signal of step 516 is preferably different than the warning signal of step 508. The early warning signal of step 516 is preferably initially of a lower intensity than the warning signal of step 508 and may be designed to increase in intensity as the predicted time within which blood-glucose concentration will be out of acceptable bounds reduces towards zero. Depending upon the configuration of the ICD 110, the warning signal may be generated by causing the pacemaker to periodically vibrate inside the patient. Alternatively or additionally, the ICD may transmit a warning signal to an external warning device such as a bedside monitor or a portable device 204 carried with the patient, which displays the warning for the patient.

The wake-up signal of 524 is similar to the warning signals of steps 508, 516 except that it is designed to arouse the patient from sleeping to wakefulness. The wake up signal may therefore be of higher intensity or different in nature than either of the warning signals of steps 508 and 516. The wake up signal of step 524 may also be transmitted to an external device such as a bedside monitor or a portable device 204 carried with the patient and then transmitted to the patient.

If a warning signal or wakeup signal is transmitted to an external device, the exact blood-glucose concentration is preferably also transmitted such that it can be displayed to the patient. Additionally, if the portable device 204 is provided with a wireless modem 732, the warning signal may also be transmitted through a communications server 709 and WAN 364, to other persons, such as the device manufacturer, a physician, clinician, nurse or caregiver as described with respect to FIG. 7. In the alternative, if an external warning device is provided, the current blood-glucose concentration may be transmitted periodically such that the patient is kept apprised of the current blood-glucose concentration. In other words, this information is not transmitted only when the blood-glucose concentration falls outside acceptable bounds but is transmitted periodically. In addition, since the blood-glucose concentration is recorded in memory at step 506, this information may be subsequently transmitted to the programmer 202 device for review by a physician during a subsequent office visit. Note that a wide range of other diagnostic information is routinely detected and recorded by the ICD 110, such as heart-rate and the like. Accordingly, the blood-glucose concentration of the patient can be correlated with other diagnostic information to help the physician develop optimal therapies for the patient and to better tune the blood-glucose concentration calculation and warning parameters.

At steps 510, 518 and 526, if an effector such as a drug pump or other therapeutic device to control blood-glucose concentration has been provided for the patient, blood-glucose analysis unit 268 transmits appropriate control signals to the effector to adjust the amount of insulin, glucagon, glucose or other agent provided to the patient or level of therapeutic intervention in response to the blood-glucose concentration and rate of change of blood-glucose concentration. For example, if the blood-glucose concentration has exceeded the upper bound, the drug pump is controlled to provide a greater amount of insulin to the patient. If the blood-glucose concentration has exceeded the lower limit, the drug pump is controlled to provide an agent, such as glucagon or glucose, to increase the blood-glucose concentration to prevent the patient from becoming hypoglycemic. As with the generation of warning signals, control of the drug pump is not limited only to circumstances in which the blood-glucose concentration has exceeded the acceptable bounds. Rather, each newly calculated value for blood-glucose concentration may be used to control the drug pump 207 to maintain the blood-glucose concentration at a target concentration deemed by the physician to be optimal such as, for example, at 100 mg/dl.

In one example, drug pump 207 is additionally controlled to modulate the blood-glucose concentration based upon the current activity level of the patient, for example, to increase the blood-glucose concentration whenever the patient is more active and to decrease it otherwise. In another example, drug pump 207 is additionally controlled to deliver insulin based on the blood-glucose concentration and the rate of change of blood-glucose concentration. Additionally, other programmable features of the ICD 110 may be adjusted based upon blood-glucose concentration and/or rate of change of blood-glucose concentration. As one example, if blood-glucose concentration is found to be particularly low, a base pacing rate may be reduced until the blood-glucose concentration returns to acceptable concentrations. A wide variety of techniques may be employed for controlling a drug pump 207 or for controlling various functions of the ICD 110 and no attempt is made herein to describe all possible techniques.

The blood-glucose concentration calculated by blood-glucose analysis unit 268 may be stored after each calculation. The stored blood-glucose concentration data may be used to generate average blood-glucose concentration figures as a measure of the quality of blood-glucose regulation over time. In one example, average blood-glucose concentration may be calculated as a running average of its value over a certain time period (e.g., can be as long as three months). The HbA1c blood test is a standard measure of average blood-glucose concentration during the previous two to three months. The average blood-glucose concentration calculated by ICD 110 over a two month to three month period can be used as a synthetic proxy for the HbA1c test and may be readily correlated to standard HbA1c test results. The average blood-glucose concentration may be calculated by ICD 110 or ICD 110 may generate and store daily blood-glucose concentration averages which can then be downloaded and averaged by programmer 202 or reader 203, or portable device 204. In this way, the overall effectiveness of blood-glucose concentration regulation can be monitored without requiring HbA1c blood tests.

Oxymetry and PPG Sensors

Figure 6A:
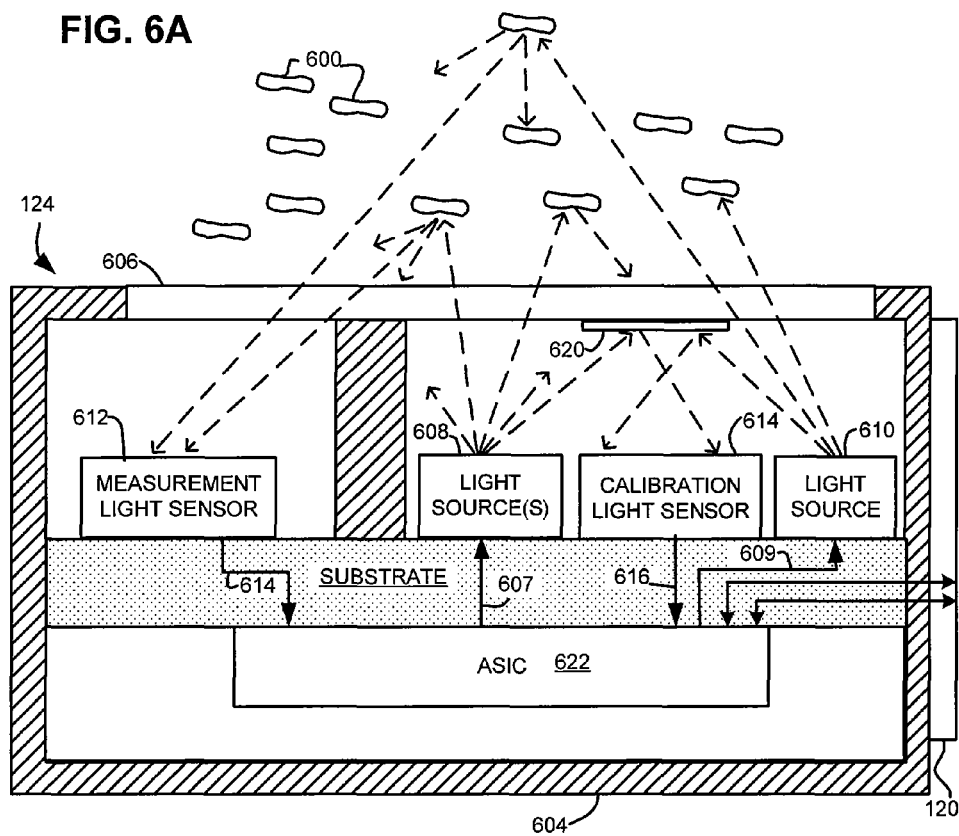
FIG. 6A shows an exemplary oxymetry sensor suitable for use in the ICD of FIGS. 1 and 2.

Referring now to FIG. 6A, there is shown an exemplary oxymetry sensor 124 suitable for measuring hematocrit in an embodiment of the present invention. In accordance with the present invention, blood-glucose concentration is determined by determining hematocrit as a proxy for measuring glucose concentration directly. An oxymeter uses light sources of two or more different centered wavelengths to obtain measures of hematocrit and blood-oxygen saturation by measuring the absorption and/or scattering of those wavelengths by oxyhemoglobin and reduced hemoglobin in the blood. The absorption and/or scattering of the light emitted by the light sources is measured using a light sensor. The absorption and/or scattering measurements can be used to measure levels of hematocrit, which refers to the percentage of packed red blood cells in a volume of whole blood.

Various techniques are known for determining hematocrit based on scattered light. In one technique, a pair of spatially separated photo detectors can be used to detect reflected infra red (IR) light, e.g., of 805 nm. The intensity of the IR light detected by the photo detector that is nearer to the IR light source is referred to as IRnear, and the intensity of the IR light detected by the photo detector farther from the IR light source is referred to as IRfar. As described in article by Bornzin et al., entitled "Measuring Oxygen Saturation and Hematocrit Using a Fiberoptic Catheter", IEEE/9th Annual Conf of the Eng. & Biol. Soc. (1997), which is incorporated herein by reference, the ratio: R=IRnear/IRfar is directly related to the level of hematocrit, but independent of oxygen saturation because 805 nm is an isobestic wavelength. Hematocrit can be measured with similar results using a single light detector, and two light sources, where one source is located closer to the light detector than the other (again producing IRnear and IRfar measurements). In another technique, light of about 500 nm and light of about 800 nm can be directed at a blood sample, and an algorithm can be used to calculate hematocrit based on the intensities of detected scattered light.

In accordance with a specific embodiment of the present invention, the implantable oxymetry sensor 124 includes an implantable housing 604 including a window 606 through which light can pass to fall on red blood cells 600. The term window, as used herein, is intended to collectively encompass all portions of the housing through which light of interest can enter and exit the housing, even if such portions are separated from one another (e.g., by opaque portions). Included within the housing are three light sources 608, one far light source 610, a measurement light sensor 612 and a calibration light sensor 614. One of each of the light sources 608 transmits light at each of the wavelengths 670 nm, 705 nm, and 805 nm. Far light source 610 transmits light at the isobestic wavelength 805 nm. The intensity of the light transmitted by each light source is controlled by a corresponding drive signal 607, 609 that drive the light sources 608 and far light source 610. The drive signal may be different for each of the three wavelengths emitted by light sources 608. A portion of the light of each wavelength exits the housing through the window 606. The measurement light sensor 612 detects light of each wavelength scattered back into the housing through the window 606, and produces a measurement signal 614 that is indicative of the intensity of the light of each wavelength detected by the measurement light sensor. A portion of window 606 above calibration sensor 614 is provided with a reflective surface 620 to reflect some but not all of the light waves onto the calibration light sensor 614. The calibration light sensor detects a portion of the light of each wavelength that has not exited the housing and produces a calibration signal 616 that is indicative of the intensity of the light of the wavelength detected by the calibration light sensor 614, which is indicative of the intensity of the light transmitted by each light source.

In accordance with specific embodiments, a controller adjusts drive signals 607, 609 based on the calibration signal 616, to keep the intensity of the light transmitted by each light source substantially constant. In accordance with other embodiments of the present invention, a controller adjusts the measurement signal 614, based on the calibration signal, to compensate for changes in the intensity of the light transmitted by each light source 608, 610. In still other embodiments, rather than adjusting signals, the oxymetry processing unit 264 (that uses the measurement signal for a diagnostic and/or therapeutic purpose) detects changes in the intensity of the light transmitted by each light source based on the calibration signal 614, and takes into account the changes in intensity when using the measurement signal 614 for a diagnostic and/or therapeutic purpose. For example, the oxymetry processing unit 264 can take such changes in intensity into account by making appropriate adjustments to algorithms that are used to determine levels of blood-oxygen saturation and/or levels hematocrit based on the measurement signal.

ASIC 622 comprises a plurality of digital to analog converters and analog to digital converters for providing the drive signals 607, 609 to drive the light sources 608 and far light source 610 and receive the measurement signal 614 and calibration signal 616. ASIC 622 communicates a digital representation of the measurement signal 614 and calibration signal 616 for each of light sources 608 and far light source 610 to ICD 110 via right atrial lead 120 and receives power from ICD 110 via right atrial lead 120. Lead 120 comprises one or more conductive wires to connect ASIC 622 to ICD 110.

More detailed descriptions of oxymetry sensors suitable for use in the present invention may be found in copending patent application U.S. Ser. No. 11/282,198 filed Nov. 17, 2005 entitled "Implantable Self Calibrating Optical Sensors" and invented by John W. Poore, which is incorporated herein by reference. Moreover, oxymetry sensor as used herein is not to be limited to the particular oxymetry sensor disclosed herein. Hematocrit may be measured by several technologies. As used herein "oxymetry sensor" should be interpreted to encompass any device or technology that can be used to determine hematocrit and optionally oxygen saturation in the blood.

Figure 6B:
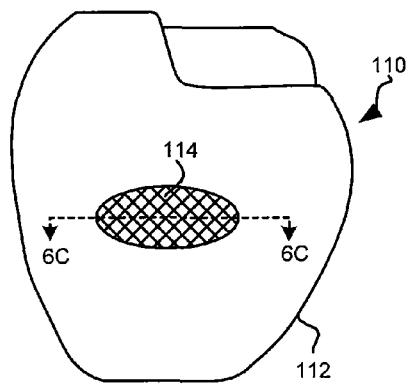
FIG. 6B shows an exemplary photoplethysmography ("PPG") sensor for use in the ICD of FIGS. 1 and 2.
Figure 6C:
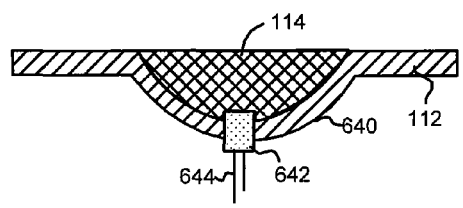
FIG. 6C shows a sectional view of the photoplethysmography sensor of FIG. 6B.

Referring now to FIGS. 6B-C which illustrate a photoplethysmography ("PPG") sensor 114 built into the housing 112 of ICD 110. FIG. 6B shows an embodiment of a PPG sensor 114 which can also be used to measure oxygen saturation. PPG sensor 114 comprises similar components to oxymetry sensor 124. Preferably, the functions of ASIC 622 of oxymetry sensor 124 are integrated into the circuitry of ICD 110 shown in FIG. 2 as PPG processing circuit 265. The electronic circuitry associated with the light source and sensor is well known for external pulse oxymeters, and is described in, e.g., U.S. Pat. No. 4,869,254 entitled, "Method And Apparatus For Calculating Arterial Oxygen Saturation" to Stone et al., and U.S. Pat. No. 5,078,136, entitled, Method And Apparatus For Calculating Arterial Oxygen Saturation Based Plethysmographs Including Transients" to Stone et al. which are incorporated herein by reference. In an exemplary embodiment the PPG sensor includes four light sources as described with respect to the oxymetry sensor of FIG. 6A. However, all that is required for the present invention is that the sensor is capable of measuring hematocrit, and this may be achieved with a single wavelength of light e.g. using the techniques disclosed in the Bornzin et al article incorporated by reference above. As shown in FIG. 6C, the PPG sensor 114 is placed in a well 640 and that is created when the monitor housing 112 is machined, formed, or cast. In the preferred embodiment well 640 is formed using the minimum volume necessary to contain its feed through connector and optical device. The remaining space in the well is filled with epoxy such that the surface of the PPG Sensor 114 is smooth and flat, thereby minimizing the risk of tissue trauma and infection. PPG sensor 114 is connected via feed-through connections 642 and 644 to PPG processing circuit 265 thus ensuring hermeticity. Additional details of implantable PPG devices suitable for use as a PPG sensor in embodiments of the present invention are disclosed in U.S. Pat. No. 6,491,639, entitled "Extravascular Hemodynamic Sensor" to Turcott, U.S. Pat. No. 6,731,967, entitled "Methods And Devices For Vascular Plethysmography Via Modulation Of Source Intensity" to Turcott, and U.S. Pat. No. 6,997,879, entitled "Methods And Devices For Reduction Of Motion-Induced Noise In Optical Vascular Plethysmography" to Turcott which are incorporated herein by reference.

Data Entry and Network Communication

Figure 7:
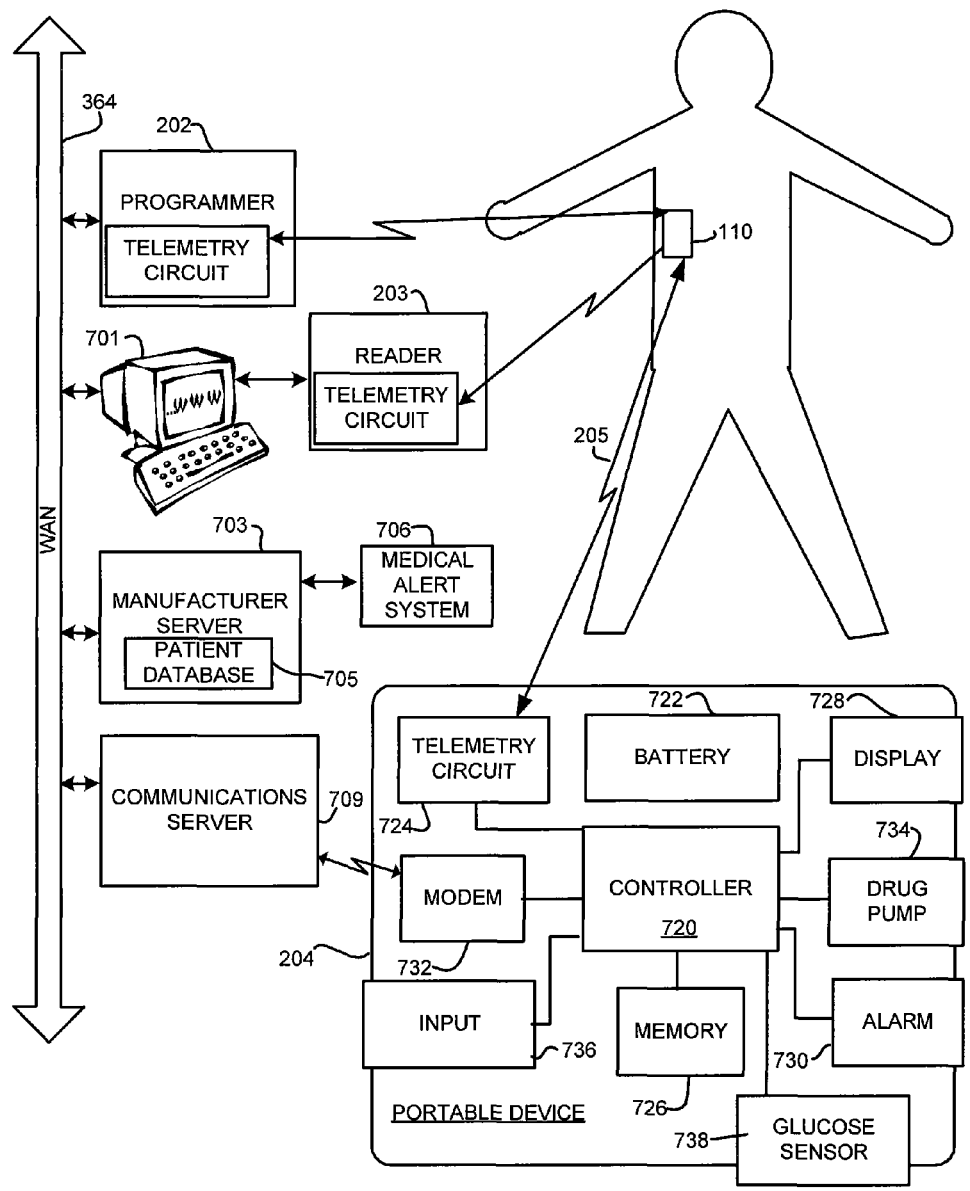
FIG. 7 shows a network communication system for use with the ICD of FIGS. 1 and 2.

Referring now to FIG. 7, where a network system comprised of the ICD 110 and a number of devices with which it may communicate are shown. As previously discussed, ICD 110 may communicate via telemetry circuit 201 with programmer 202. In addition, the patient may be provided with a reader 203 which has its own telemetry circuit which may receive information from ICD 110. Reader 203 may be, for example, a peripheral device connected to a patient's general purpose computer. Computer system 701 preferably comprises software for initiating transfer of data via reader 203 from ICD 110. The software should also be able to accept data input by the patient using a standard computer keyboard. For example, the patient might be asked to keep a diary of foods consumed, exercise undertaken, subjective energy levels and qualitative feelings of healthfulness.

The information entered by the patient may be correlated with the records of blood-glucose concentration and other physiological data downloaded from the ICD 110. Based on correlations between the patient-entered data and the physiological data and calculated blood-glucose concentrations, the computer system could provide advice to the patient as to how to better maintain blood-glucose concentration. In addition, computer system 701, if provided with a modem or NIC, can communicate the patient entered data and downloaded blood-glucose concentration onto a Wide Area network (WAN) 364. WAN 364 may communicate the data to the computer system of a physician, healthcare provider, or the manufacturer of the ICD. One way to achieve this is for computer system 701 to communicate the data to manufacturer server 703. Manufacturer server 703 includes a patient database 704 which provides information regarding the patient and ICD 110, including communication addresses for the physicians, healthcare providers and caregivers of the patient. Manufacturer server 703 can then forward the data to the individuals identified in the patient database via the WAN 364. For example, the data may be forwarded to programmer 202 under the control of a physician where the data can be used to readjust the programmed parameters of ICD 110 upon the patient's next visit to the physician. In addition, should the data indicate a serious and immediate problem, the manufacturer server 703, may instead communicate the data and patient data to Medical Alert System 706 which may act by multiple communication channels, such as paging, telephone etc to contact the physician, clinician, nurse, or caregiver of the patient to alert them of said serious an immediate problem or contact emergency services.

Alternatively or additionally, the patient may carry portable device 204. Portable device 204 may have the same general components as a wireless PDA with the addition of a telemetry circuit 724 for receiving information from ICD 110. As shown in FIG. 7, portable device 204 comprises a controller 720, battery 722, telemetry circuit 724, memory 726, display 728, alarm 730, and wireless modem 732. Portable device 204 may also include an external drug pump 734 for supplying e.g. insulin, glucagon or glucose to the patient if the patient does not have an implantable drug pump 207. Portable device 204 may also optionally include a blood-glucose sensor 738. Blood-glucose sensor 738 can measure the patient's blood-glucose concentration using standard methods such as the hexokinase method and transmit the blood-glucose concentration to ICD 110. Where portable device 204 has an external blood-glucose sensor, portable device 204 may perform the functions of external blood-glucose monitor 204 as shown in FIG. 4B. Portable device 204 may thus perform the functions of external blood-glucose monitor 200.

Portable device 204 is carried by the patient close to ICD 110 to allow for reliable communication with ICD 110 via telemetry circuit 724. The communication may be initiated by the portable device—with or without user intervention or by ICD 110. Blood-glucose concentration information and other physiological data may be downloaded from ICD 111 to portable device 204. In addition, portable device 204 preferably comprises data entry means by which the patient may enter subjective health or other data. The downloaded and entered information may then by transmitted via the wireless modem to a communication server and thence via WAN 364 to the manufacturer server 705. This data may be forwarded by manufacturer server 703 in the same way as previously discussed. In addition, in certain circumstances, it may be desirable to upload external data from the portable device 204 to the ICD 111 over a communication link 205. Such external data may include, for example, data entered by the patient, caregiver or physician indicating well-being, activity level, consumption of food or administration of insulin. For example, the patient may enter data indicating that the patient is going to sleep and how many hours the patient expects to be asleep. This data may be used by the blood-glucose analysis unit to determine whether the patient will enter hypoglycemia before waking. Other external data could also include for example, data from sensors included in or connected to the portable device, such as temperature sensors, pulse sensors, light sensors and the like. ICD 111 may use such external data as input into the calculation of glucose concentration or to modify the parameters or to adjust the thresholds for alerts.

Additionally, portable device 204 may display blood-glucose concentration to the patient and thus advise the patient for example, whether a hypoglycemic event is imminent and thus to consume something to raise the blood-glucose concentration. Portable device 204 is preferably provided with an alarm 730 which is a device such as a vibrator, beeper or flashing light to draw attention of the patient to the portable device in order to provide information or to wake up the patient if necessary. Where blood-glucose concentrations are provided on a regular basis to portable device 204, steps 504-526 of FIG. 5 may be performed by the portable device 204 including providing the warnings of steps 510 and 518 and the wake up signal of step 524.

The previous description of the preferred embodiments is provided to enable any person skilled in the art to make or use the embodiments of the present invention. While the previous description has described an embodiment of the present invention which includes cardiac stimulation abilities as well as blood-glucose concentration measurement, it is to be understood that a stand alone blood-glucose concentration measurement device may be made without departing from the spirit and scope of the invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring blood-glucose concentration of a patient using an implantable medical device, the method comprising:
   (a) measuring hematocrit using an implantable sensor;
   (b) determining a plurality of hematocrit values at a plurality of times;
   (c) comparing the plurality of hematocrit values determined at the plurality of times to monitor a change in hematocrit;
   (d) determining, using a processor, a change in blood-glucose concentration using the change in hematocrit;
   (e) determining a rate of change in hematocrit from the change in hematocrit over a period of time; and
   (f) using the rate of change in hematocrit to determine a rate of change of blood-glucose concentration.

2. The method of claim 1, wherein the method further comprises:
   obtaining a blood-glucose calibration value from a blood-glucose sensor;
   and using the change in hematocrit and the blood-glucose calibration value to determine the change in blood-glucose concentration and generate a subsequent blood-glucose concentration value.

3. The method of claim 2, wherein the blood-glucose sensor is a component of a blood-glucose concentration measurement device external to the patient and wherein the method further comprises wirelessly receiving the blood-glucose calibration value from the blood-glucose concentration measurement device.

4. The method of claim 1, further comprising: generating an alert that can be sensed by the patient if the blood-glucose concentration value is indicative of hypoglycemia or hyperglycemia.

5. The method of claim 1, wherein the implantable medical device comprises:
   a therapeutic device,
   and wherein the method further comprises controlling the therapeutic device in response to the blood-glucose concentration value to change the concentration of glucose in the blood if the blood-glucose concentration value is indicative of hypoglycemia or hyperglycemia.

6. The method of claim 1, wherein the implantable medical device provides electrical stimulation to an organ of the patient according to parameters, and wherein the method comprises:
   causing a change in the parameters of the electrical stimulation provided to the organ in response to the change in blood-glucose concentration.

7. The method of claim 1, wherein the implantable medical device comprises a blood-glucose elevating system, and wherein the method further comprises:
   causing the blood-glucose elevating system to elevate the blood-glucose concentration of the patient if the change in blood-glucose concentration is indicative of hypoglycemia.

8. The method of claim 1, wherein the implantable medical device is in communication with an arousal device capable of waking up the patient, and wherein the method further comprises:
   triggering the arousal device if the change in blood-glucose concentration is indicative of hypoglycemia.

9. The method of claim 1, wherein the implantable medical device comprises a blood-glucose elevating system, and wherein the method further comprises:
   causing the blood-glucose elevating system to elevate the blood-glucose concentration of the patient if the change in blood-glucose concentration is indicative of increased risk of hypoglycemia-induced arrhythmia.

10. A system for monitoring blood-glucose concentration in a patient, comprising:
    an implantable hematocrit sensor that monitors changes in hematocrit and determines a rate of change in hematocrit;
    and a blood glucose monitor that determines changes in blood-glucose concentration using the rate of change in hematocrit monitored by the implantable hematocrit sensor.

11. The system of claim 10, further comprising:
    an effector that controls one or more of application of a therapy and communication of a diagnosis in response to the changes in blood-glucose concentration.

12. The system of claim 10, further comprising:
    a warning system that is configured to deliver, automatically, an alert if the changes in blood-glucose concentration are indicative of hypoglycemia;
    and wherein the warning system delivers the alert to one or more of the patient, a physician, a clinician, a nurse, a manufacturer, and a caregiver.

13. The system of claim 10, further comprising:
    an effector that automatically increases the blood-glucose concentration of the patient if the changes in blood-glucose concentration are indicative of hypoglycemia.

14. The system of claim 10, further comprising:
    an arousal system is configured to cause the patient to wake up if the patient is sleeping and the changes in blood-glucose concentration are indicative of an elevated risk of hypoglycemia-induced arrhythmia.

15. The system of claim 10, wherein:
    the blood-glucose monitor and implantable hematocrit sensor are part of an implantable medical device; and
    wherein the system further comprises an external blood-glucose monitor that determines a blood-glucose calibration value and transmits the blood-glucose calibration value to the implantable medical device.

16. A system for monitoring blood-glucose level, comprising:
    a calibration sensor for measuring a first blood-glucose value;
    a memory for storing the first blood-glucose value;
    a hematocrit sensor for measuring a rate of change in hematocrit;
    and a monitor for determining a second blood-glucose value based on the first blood-glucose value and the rate of change in hematocrit.

17. They system of claim 16, wherein:
    the calibration sensor is configured to be external to the patient;
    the hematocrit sensor is implantable in the patient;
    and the calibration sensor is at least intermittently in communication with the monitor via a wireless communication link.

* * * * *